(12) United States Patent
Zhang et al.

(10) Patent No.: US 11,247,966 B2
(45) Date of Patent: Feb. 15, 2022

(54) 4-(P-TRIFLUOROMETHYLBENZYL)-3-FLUORO-1,2,4-TRIPHENYLAMINE DERIVATIVE AND PHARMACEUTICAL COMPOSITION AND APPLICATIONS THEREOF

(71) Applicant: HEBEI MEDICAL UNIVERSITY, Shijiazhuang (CN)

(72) Inventors: Hailin Zhang, Shijiazhuang (CN); Jinlong Qi, Shijiazhuang (CN); Qingzhong Jia, Shijiazhuang (CN); Xiaona Du, Shijiazhuang (CN); Han Hao, Shijiazhuang (CN)

(73) Assignee: HEBEI MEDICAL UNIVERSITY, Shijiazhuang (CN)

( * ) Notice: Subject to any disclaimer, the term of this patent is extended or adjusted under 35 U.S.C. 154(b) by 0 days.

(21) Appl. No.: 17/253,639

(22) PCT Filed: Jun. 14, 2019

(86) PCT No.: PCT/CN2019/091365
§ 371 (c)(1),
(2) Date: Dec. 18, 2020

(87) PCT Pub. No.: WO2020/001298
PCT Pub. Date: Jan. 2, 2020

(65) Prior Publication Data
US 2021/0269392 A1 Sep. 2, 2021

(30) Foreign Application Priority Data
Jun. 29, 2018 (CN) .......................... 201810716419.5

(51) Int. Cl.
*C07C 233/88* (2006.01)
*C07C 231/14* (2006.01)
*C07C 231/24* (2006.01)

(52) U.S. Cl.
CPC .......... *C07C 233/88* (2013.01); *C07C 231/14* (2013.01); *C07C 231/24* (2013.01); *C07C 2601/16* (2017.05)

(58) Field of Classification Search
CPC .......................... C07C 233/88; C07C 231/14
See application file for complete search history.

(56) References Cited

FOREIGN PATENT DOCUMENTS

| CN | 1761464 A | 4/2006 |
|---|---|---|
| CN | 101056845 A | 10/2007 |
| CN | 101790374 A | 7/2010 |
| CN | 108707087 A | 10/2018 |
| WO | 2016077724 A1 | 5/2016 |

OTHER PUBLICATIONS

Thornber, Chem. Soc. Rev., 1979, 563-580.*
Michael C. Sanguinetti, Dysfunction of Delayed Rectifier Potassium Channels in an Inherited Cardiac Arrhythmia, Annals New York Academy of Sciences, pp. 406-413.
Snezana Maljevic et al., Nervous system KV7 disorders: breakdown of a subthreshold brake, Symposium Report, The Journal of Physiology, 2008, pp. 1791-1801, 586(7).
M. Bialer et al., Progress report on new antiepileptic drugs: a summary of the Sixth Eilat Conference (EILAT VI), Epilepsy Research, 2002, pp. 31-71, 51(1-2).

* cited by examiner

*Primary Examiner* — Ana Z Muresan
(74) *Attorney, Agent, or Firm* — Bayramoglu Law Offices LLC

(57) ABSTRACT

A 4-(p-trifluoromethylbenzyl)-3-fluoro-1,2,4-triphenylamine derivative, a pharmaceutical composition and applications thereof are disclosed. The general chemical formula of the derivative is shown in formula I, where, R is a $C_1$-$C_6$ alkyl group, a cycloalkyl group, a heteroatom-containing cycloalkyl group, an aryl group or a heteroatom-containing aryl group, the heteroatom is selected from N or O, and the n is 0, 1, 2 or 3. The pharmaceutical composition contains any one of the above-mentioned 4-(p-trifluoromethylbenzyl)-3-fluoro-1,2,4-triphenylamine derivatives as an active ingredient, and one or more pharmaceutically acceptable carriers. The derivative and the pharmaceutical composition activate KCNQ channel currents. Thus, the derivative can be applied to prepare a KCNQ potassium channel opener, and can be used as the active ingredients of an antiepileptic pharmaceutical preparation, an antianxiety pharmaceutical preparation and a neuropathic pain-relieving pharmaceutical preparation.

8 Claims, 2 Drawing Sheets

4-(P-TRIFLUOROMETHYLBENZYL)-3-FLUORO-1,2,4-TRIPHENYLAMINE DERIVATIVE AND PHARMACEUTICAL COMPOSITION AND APPLICATIONS THEREOF

CROSS REFERENCE TO THE RELATED APPLICATIONS

This application is the national phase entry of International Application No. PCT/CN2019/091365, filed on Jun. 14, 2019, which is based upon and claims priority to Chinese Patent Application No. 201810716419.5, filed on Jun. 29, 2018, the entire contents of which are incorporated herein by reference.

TECHNICAL FIELD

The present invention relates to a compound, a pharmaceutical composition containing the compound and medical applications thereof, and in particular to a 4-(p-trifluoromethylbenzyl)-3-fluoro-1,2,4-triphenylamine derivative, a pharmaceutical composition thereof and applications thereof in preparing a KCNQ potassium channel opener, an antiepileptic pharmaceutical preparation and an analgesic pharmaceutical preparation.

BACKGROUND

The Potassium voltage-gated channel subfamily Q (KCNQ) is an important branch of the potassium channel family. Currently, numerous types of KCNQ potassium channels are available on various types of cells. According to the structural characteristics, KCNQ potassium channels are mainly divided into five categories, including KCNQ1, KCNQ2, KCNQ3, KCNQ4 and KCNQ5. KCNQ1 (also known as KvLQT) is mainly distributed in the heart; KCNQ2-5 are mainly distributed in the central and peripheral nervous system, inner ear (KCNQ4), muscle tissue (KCNQ5), etc. Studies have confirmed that KCNQ1 and KCNE1 co-encode to form the slowly activating delayed rectifier potassium channel ($I_{Ks}$) in the myocardium, and mutations of the $I_{Ks}$ cause hereditary long-QT syndrome (LQT, Sanguinetti M C, Ann NY. Acad Sci. 1999, 868: 406-13).

KCNQ4 gene encodes the molecules related to potassium channels in cochlear outer hair cells and vestibular organ type I hair cells, and mutations of the KCNQ4 gene, which causes hereditary deafness. The current produced by co-expression of KCNQ2 and KCNQ3 channels is the molecular basis of M-type potassium current in neurons, and M-channel plays an essential role in regulating the excitability of nerve cells. Changes of M-channel function induced by KCNQ2/Q3 gene mutations may lead to neurologic diseases such as benign familial neonatal convulsion (BFNC) (Maljevic S et al., J Physical. 2008, 586(7): 1791-801). KCNQ2/3 channel opener can reduce neuronal excitability and can be used to treat diseases related to neuronal hyperexcitability, such as convulsion, epilepsy and neuropathic pain.

Epilepsy is a common and frequently-occurring nervous system disease characterized by sudden, transient and recurrent seizures caused by abnormal discharges of cerebral neurons, which seriously threatens human life and health. Clinical treatment of epilepsy relies mostly on drug therapy. Currently, the only KCNQ potassium channel agonist drug approved by FDA for partial episode adjuvant therapy in adults is retigabine, which has certain anticonvulsant properties in vivo and in vitro, and has the effect of reducing the incidence rate of seizures (Bialer et al., Epilepsy Research. 2002, 52, 31-71). The post-marketing retigabine, however, is evaluated to have side effects such as dizziness, drowsiness, tremor and other neurological symptoms and urinary retention, and its effect needs further verification. Therefore, it is of great significance to find and develop novel KCNQ potassium channel openers with increased activity and better selectivity, and further develop novel, safe and effective antiepileptic and analgesic drugs that may provide more choices for clinical medication.

SUMMARY

The first objective of the present invention is to provide a 4-(p-trifluoromethylbenzyl)-3-fluoro-1,2,4-triphenylamine derivative.

The second objective of the present invention is to provide a preparation method of the 4-(p-trifluoromethylbenzyl)-3-fluoro-1,2,4-triphenylamine derivative.

The third objective of the present invention is to provide a composition containing the 4-(p-trifluoromethylbenzyl)-3-fluoro-1,2,4-triphenylamine derivative.

The fourth objective of the present invention is to provide an application of the 4-(p-trifluoromethylbenzyl)-3-fluoro-1,2,4-triphenylamine derivative in preparing a KCNQ potassium channel opener, especially applications in preparing an antiepileptic pharmaceutical preparation, an antianxiety pharmaceutical preparation and a neurogenic pain-relieving pharmaceutical preparation, so as to provide more medication choices for clinical treatments.

The first objective of the present invention is achieved as follows.

The 4-(p-trifluoromethylbenzyl)-3-fluoro-1,2,4-triphenylamine derivative has a general chemical formula shown in formula I:

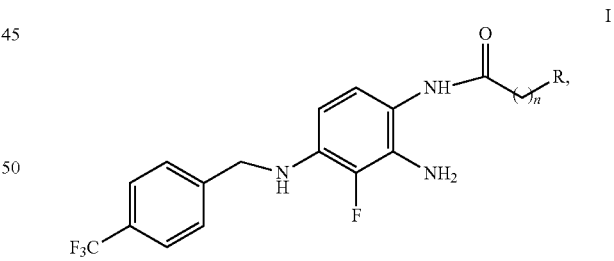

where, R is a $C_1$-$C_6$ alkyl group, a cycloalkyl group, a heteroatom-containing cycloalkyl group, an aryl group or a heteroatom-containing aryl group, the heteroatom is selected from N or O, and n iso, 1, 2 or 3.

Preferably, the alkyl group is methyl, ethyl or tert-butyl, the cycloalkyl group is cyclopentyl or cyclohexyl, the heteroatom-containing cycloalkyl group is piperidinyl, the aryl group is phenyl, and the heteroatom-containing aryl group is furanyl.

More preferably, R is cyclopentyl, n=1, and the structural formula of the compound is as follows:

Compound 1

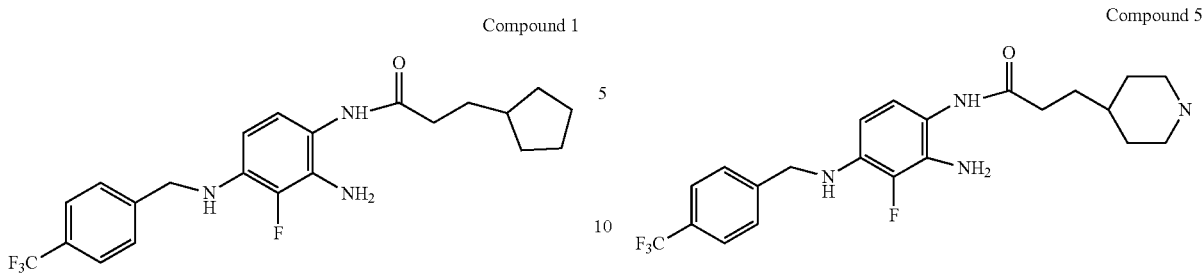

More preferably, R is tert-butyl, n=0, and the structural formula of the compound is as follows:

Compound 2

More preferably, R is cyclopentyl, n=0, and the structural formula of the compound is as follows:

Compound 3

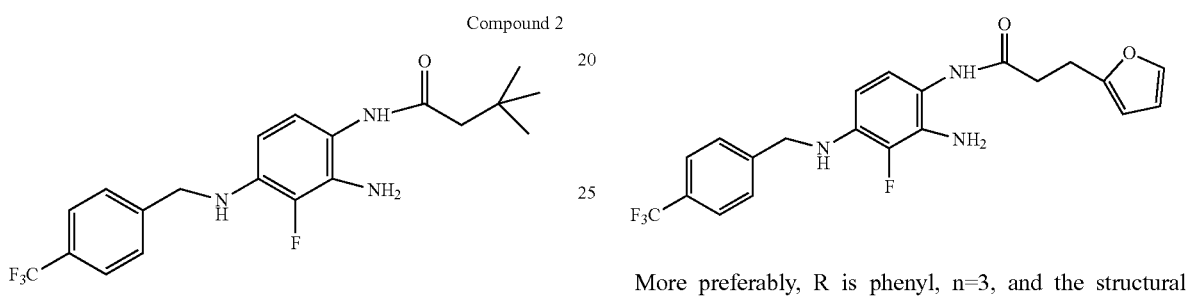

More preferably, R is cyclopentyl, n=1, and the structural formula of the compound is as follows:

Compound 4

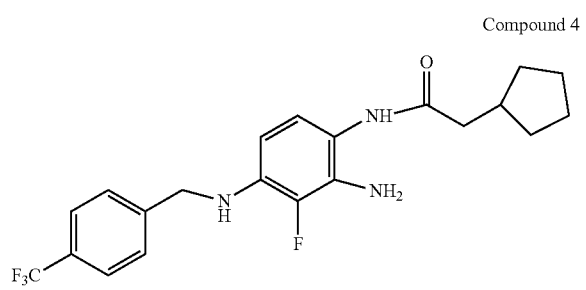 [SMILES: Nc1c(NC(=O)CC2CCCC2)ccc(NCc2ccc(C(F)(F)F)cc2)c1F]

More preferably, R is piperidinyl, n=2, and the structural formula of the compound is as follows:

Compound 5

More preferably, R is furanyl, n=2, and the structural formula of the compound is as follows:

Compound 6

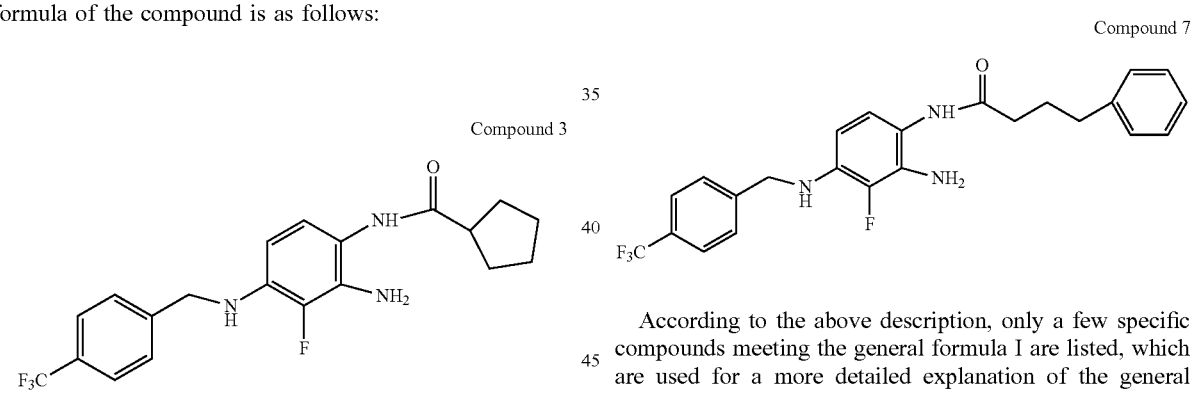

More preferably, R is phenyl, n=3, and the structural formula of the compound is as follows:

Compound 7

According to the above description, only a few specific compounds meeting the general formula I are listed, which are used for a more detailed explanation of the general formula I and its substituents, but they are not exhaustive of the compounds of the present invention.

The compound disclosed in the present invention can exist in a form of a free alkali or a salt. When the compound exists in the form of the free base, in application, physiologically acceptable inorganic acids (such as hydrochloric acid, sulfuric acid, hydrobromic acid, hydroiodic acid, phosphoric acid) and organic acids (such as acetic acid, propionic acid, citric acid, maleic acid, malic acid, tartaric acid, methanesulfonic acid) can be selected to form the salt.

The second objective of the present invention is achieved as follows.

The preparation method of the 4-(p-trifluoromethylbenzyl)-3-fluoro-1,2,4-triphenylamine derivative includes the following steps:

(a) dissolving p-trifluoromethyl benzylamine and 2,3-difluoro-6-nitroaniline in anhydrous dimethyl sulfoxide (DMSO) for a reaction under conditions of triethylamine as an acid-binding agent and iodine as a catalyst, to obtain an intermediate III, namely 2-fluoro-4-nitro-$N^1$-(4-trifluoromethyl-benzyl)-1,3-phenylenediamine;

(b) putting the 2-fluoro-4-nitro-$N^1$-(4-trifluoromethyl-benzyl)-1,3-phenylenediamine (intermediate III) into a zinc powder saturated ammonium chloride system for a reduction reaction to obtain an intermediate II, namely 3-fluoro-N4-(4-trifluoromethyl-benzyl)-1,2,4-benzenetriamine;

(c) dissolving the 3-fluoro-N4-(4-trifluoromethyl-benzyl)-1,2,4-benzenetriamine (intermediate II) and a corresponding R-substituted carboxylic acid in a solvent, adding 1-ethyl-3-(3-dimethylaminopropyl)carbodiimide hydrochloride (EDC.HCl) and 4-dimethylaminopyridine (DMAP) therein for a reaction, separating a liquid after the reaction is ended, and extracting the target compound I from an organic layer.

The synthetic reaction formula is as follows.

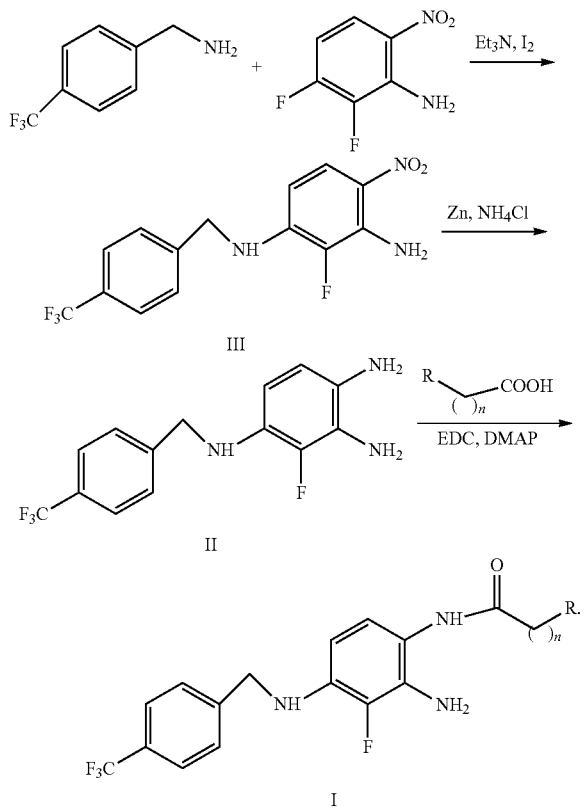

In step (c), a molar ratio of the 3-fluoro-N4-(4-trifluoromethyl-benzyl)-1,2,4-benzenetriamine (intermediate II), the R-substituted carboxylic acid, the EDC.HCl and the DMAP is 1:1:1-2:0.1-1.

Preferably, the molar ratio of the 3-fluoro-N4-(4-trifluoromethyl-benzyl)-1,2,4-benzenetriamine (intermediate II), the R-substituted carboxylic acid, the EDC.HCl and the DMAP is 1:1:2:0.5.

The third objective of the present invention is achieved as follows.

The composition containing the 4-(p-trifluoromethylbenzyl)-3-fluoro-1,2,4-triphenylamine derivative includes any one of the above-mentioned 4-(p-trifluoromethylbenzyl)-3-fluoro-1,2,4-triphenylamine derivatives as an active ingredient and one or more pharmaceutically acceptable carriers. The pharmaceutically acceptable carriers or diluents are selected from excipients, adjuvants or solvents commonly used in pharmaceutical preparations, such as lactose, sucrose, dextrin, talc powder, gelatin, agar, pectin, gum Arabic, magnesium stearate, stearic acid, lower alkyl ethers of cellulose, corn starch, potato starch, gum, syrup, peanut oil, olive oil, phospholipid, fatty acid, fatty acid amine, glycerol monostearate or glycerol distearate, colorant, flavoring agent, preservative, water, ethanol, propanol, normal saline and glucose solution.

The specific preparation method of the composition can be carried out according to the preparation method of conventional preparations. For example, the compound of the present invention can be used as the active ingredient to be prepared into an oral liquid preparation with water, sucrose, sorbitol, fructose, etc.; the compound of the present invention can also be prepared into tablets or capsules with lactose, glucose, sucrose, mannitol, etc. as excipients, starch and the like as disintegrating agents, stearic acid and talc powder as lubricants, and gelatin and polyvinyl alcohol as binding agents; the compound of the present invention can be prepared into an injectable liquid with normal saline, glucose solution, or a mixed carrier consisting of normal saline and glucose solution; alternatively, the compound of the present invention can be prepared into sterile powder injection, various sustained-release agents, suspensions, emulsions, etc.

The fourth objective of the present invention is achieved as follows.

The 4-(p-trifluoromethylbenzyl)-3-fluoro-1,2,4-triphenylamine derivative provided by the present invention can be applied to prepare the KCNQ potassium channel opener. The derivative obviously activates KCNQ2 and KCNQ3 channel currents, but has no obvious activation effect on KCNQ4 and KCNQ5, and therefore has substantial channel selectivity.

The 4-(p-trifluoromethylbenzyl)-3-fluoro-1,2,4-triphenylamine derivative provided by the present invention can also be applied to prepare the antiepileptic pharmaceutical preparation. The derivative can be used as the active ingredient of the antiepileptic pharmaceutical preparation for preventing, suppressing, alleviating and treating convulsion, epileptic seizure, epileptic status and epilepsy syndrome.

The 4-(p-trifluoromethylbenzyl)-3-fluoro-1,2,4-triphenylamine derivative provided by the present invention can also be applied to prepare the antianxiety pharmaceutical preparation. The derivative can be used as the active ingredient of the antianxiety pharmaceutical preparation to relieve anxiety symptoms.

The 4-(p-trifluoromethylbenzyl)-3-fluoro-1,2,4-triphenylamine derivative provided by the present invention can also be applied to prepare the analgesic pharmaceutical preparation. The derivative can be used as the active ingredient of the analgesic pharmaceutical preparation to relieve neuropathic pain.

Further, the 4-(p-trifluoromethylbenzyl)-3-fluoro-1,2,4-triphenylamine derivative and its pharmaceutical preparations provided by the present invention are safer compared with the positive control drug: retigabine available on the market.

The pharmaceutical preparations prepared from the compound of the present invention can be administered orally or non-orally. The dosage varies with a dosage form, a dosage frequency, a dosage mode, a disease course, individual differences and health status of patients. For adults, 4-40 mg/day is suitable, and physicians can make necessary adjustments according to the actual clinical situation.

According to a toxicological test, the compound of the present invention has not obtained the hint of obvious toxic effect on human body.

DETAILED DESCRIPTION OF THE EMBODIMENTS

Figure 1:
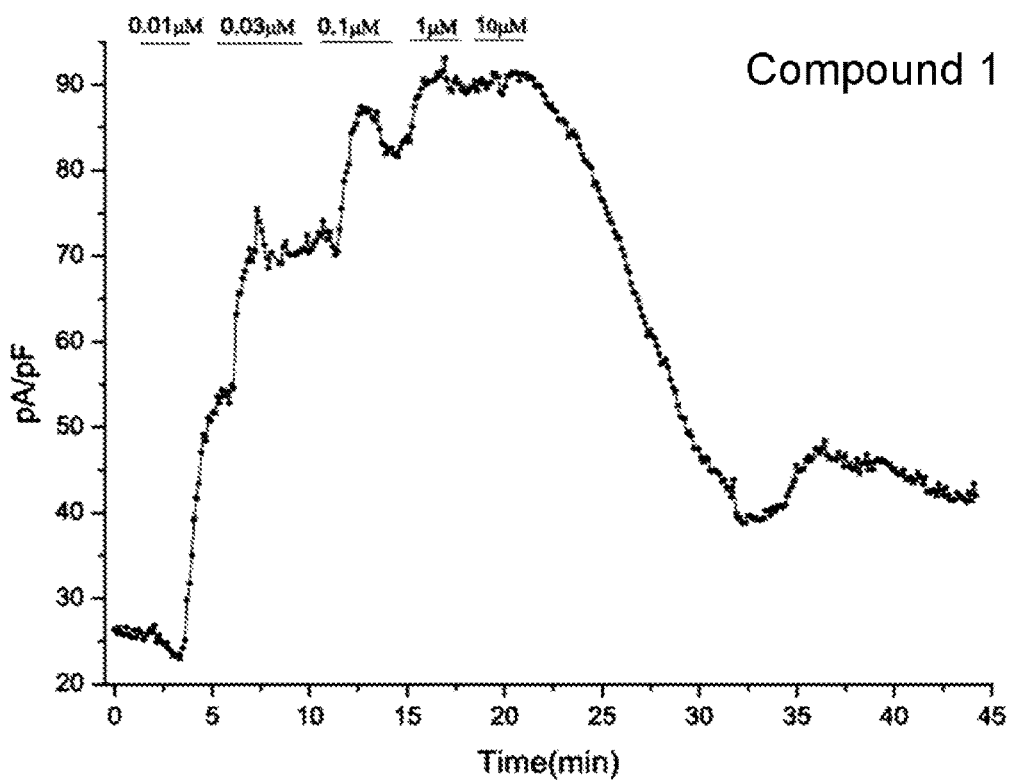
FIG. 1 is a diagram showing a time course of an opening effect of a compound 1 on KCNQ2/3 channels recorded by a whole-cell patch clamp.

The present invention is further described in combination with embodiments. The following embodiments are only for illustration and do not limit the protection scope of the present invention in any way.

The reagents used in the embodiments are all analytically pure or chemically pure, and can be purchased through commercial channels or prepared by methods well known to ordinary technical personnel in the art. The following embodiments all achieve the objectives of the present invention.

In the present invention, compounds with the same number are the same compound.

The derivative described in the general formula I is synthesized by the following general synthetic route, and the specific steps are as follows:

(1) p-trifluoromethyl benzylamine and 2,3-difluoro-6-nitroaniline are dissolved in anhydrous DMSO for a reaction overnight under conditions of triethylamine as an acid-binding agent and trace iodine as a catalyst, to obtain a yellow solid intermediate III;

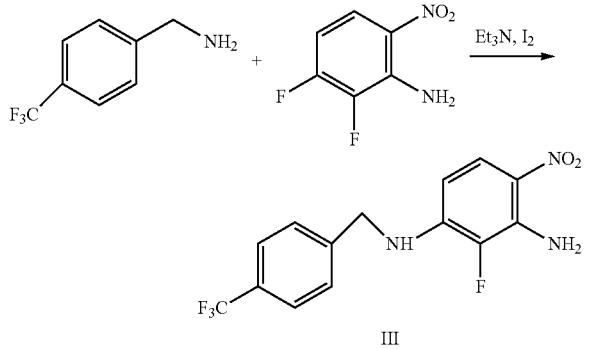

(2) the intermediate III is put into a zinc powder saturated ammonium chloride system for a reduction reaction overnight with vigorous stirring at room temperature, filtered by diatomite, washed, and a solvent is recovered to obtain a dark red solid intermediate II, which can be directly used for the next reaction without being purified;

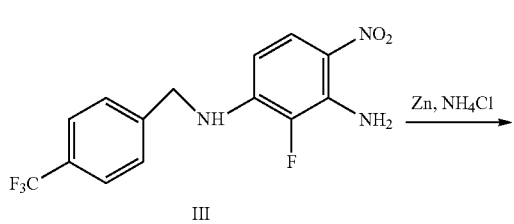

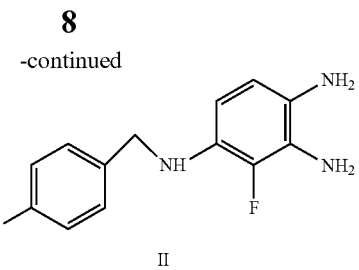

(3) the intermediate II and a corresponding R-substituted carboxylic acid are dissolved in anhydrous dichloromethane, EDC.HCl and DMAP are added under stirring for a reaction overnight, water is added to terminate the reaction, then a liquid is separated, an organic layer is repeatedly washed and a solvent is recovered, followed by passing through a silica gel chromatographic column or recrystallizing with a predetermined amount of a dilute alcohol solution to obtain a target compound I;

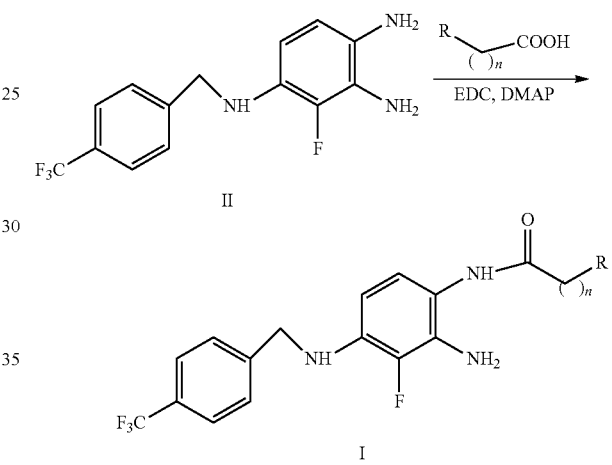

where, substituent R is a short-chain aliphatic hydrocarbon or a cycloalkane, and a molar ratio of the compound II, the R-substituted carboxylic acid, the EDC.HCl and the DMAP is 1:1:1-2.5:0.1-1, preferably 1:1:2:0.5.

Embodiment 1

The compound 1 (N-(2-amino-3-fluoro-4-(4-trifluoromethylbenzylamino)-phenyl)-cyclopentyl propionamide) is prepared according to the above-mentioned preparation method of the compound having the general formula, and the specific steps are as follows.

(1) Synthesis of the Intermediate III (2-fluoro-4-nitro-$N^1$-(4-trifluoromethyl-benzyl)-1,3-phenylene-diamine)

P-trifluoromethyl benzylamine (2.43 ml, 16.7 mmol) and 2,3-difluoro-6-nitroaniline (3 g, 16.7 mmol) are dissolved in 70 ml of anhydrous DMSO, followed by adding triethylamine (2.7 ml, 20.1 mmol) and elemental iodine (50 mg) as catalysts, to obtain a reaction mixture; the reaction mixture reacts at 120° C. for 24 h, followed by being cooled to room temperature, diluted with 200 ml of water, extracted with ethyl acetate for 3 times (100 ml×3); an organic layer is dried with anhydrous magnesium sulfate, and a solvent is recovered under a reduced pressure; and a filter cake is washed with a petroleum ether/ethyl acetate (5:1) mixed solvent to obtain 3.71 g of a yellow solid with a yield of 67.3%, a melting point of 165.0-166.5° C., and a mass spectroscopic analysis of [M+H]$^+$ 330.1.

(2) Synthesis of the Intermediate II (3-fluoro-N4-(4-trifluoromethyl-benzyl)-1,2,4-benzenetriamine)

Zinc powder (3.3 g, 50 mmol) is added to a methanol solution (50 ml) of the intermediate III (3.3 g, 10 mmol), and then a saturated ammonium chloride solution (10 ml) is added; a reaction mixture is stirred vigorously at room temperature for 5 h until the yellow color of the reaction mixture is almost completely faded; the resulting mixture is filtered with a silica gel, and a filter cake is fully washed with ethyl acetate; after methanol is recovered from a filtrate, a predetermined amount of water is added, followed by extracting with ethyl acetate for 3 times (50 ml×3); ethyl acetate layers are combined and dried with anhydrous sodium sulfate, and a solvent is recovered to obtain 2.5 g of a dark red solid with a yield of 83%, [M+H]$^+$ 300.1, and a purity of more than 96% detected by high performance liquid chromatography (HPLC); and the dark red solid is directly used for the next reaction without being purified.

(3) Synthesis of the Compound 1

The intermediate II (1.52 g, 5 mmol) and 3-cyclopentyl propionic acid (0.72 ml, 5 mmol) are dissolved in dry dichloromethane (20 ml), and EDC.HCl (1.2 g, 10 mmol) and DMAP (0.4 g, 2.5 mmol) are added for a reaction overnight at room temperature under stirring; after the reaction, a reaction solution is fully washed with water (20 ml×3) and dichloromethane is recovered under a reduced pressure; and an obtained solid is eluted with absolute ethanol to obtain 1.75 g of a white solid substance (compound 1) with a yield of 81.4%.

Compound 1

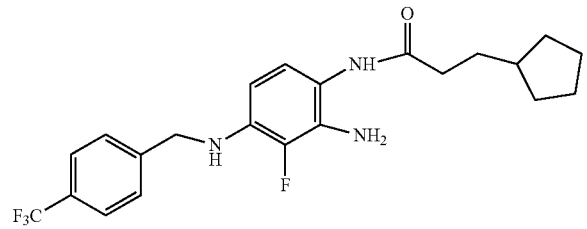

The white solid substance has a melting point of 203-205° C.; an electrospray ionization (ESI) mass spectroscopic analysis of [M+H]$^+$ 424.2, $^1$H-NMR (500 MHz, DMSO-d6) &: 1.46-1.76 (m, 9H, Cyclopentyl-H), 1.08 (d, 2H, —C=OCH$_2$C$\underline{H}_2$), 2.25 (t, 2H, C=OC$\underline{H}_2$CH$_2$), 4.38 (d, 2H, C$\underline{H}_2$NH), 4.58 (s, 2H, NH$_2$), 5.77 (t, 1H, CH$_2$N$\underline{H}$), 6.02 (t, 1H, Ph-H), 6.57 (d, 1H, Ph-H), 7.54 (d, 2H, Ph-H), 7.66 (d, 2H, Ph-H), 8.98 (s, 1H, C=ON$\underline{H}$); $^{13}$C-NMR (125 MHz, DMSO-d6) &: 25.19 (Cyclopentyl CH$_2$), 32.52 (Cyclopentyl CH$_2$), 32.08 (CH$_2$) 35.41 (COCH$_2$), 46.16 (Cyclopentyl CH), 100.06 (CH$_2$NH), 127.34 (CF$_3$), 171.98 (C=O), 146.22 (CF), 141.61 (Ph-C), 139.79 (Ph-C), 134.40 (Ph-C), 131.42 (Ph-C), 127.90 (Ph-C), 125.96 (Ph-C), 125.56 (Ph-C) 123.80 (Ph-C) 121.51 (Ph-C) 115.57 (Ph-C).

Embodiment 2

Synthesis of the Compound 2 (N-(2-amino-3-fluoro-4-(4-trifluoromethyl benzylamino)-phenyl)-3,3-dimethyl Butyramide The intermediate II (1.52 g, 5 mmol) and 3,3-dimethyl-butyric acid (0.625 ml, 5 mmol) are dissolved in dry dichloromethane (20 ml), and EDC.HCl (1.2 g, 10 mmol) and DMAP (0.4 g, 2.5 mmol) are added for a reaction overnight at room temperature under stirring; after the reaction, a reaction solution is fully washed with water (20 ml×3) and dichloromethane is recovered under a reduced pressure; and an obtained solid is recrystallized with dilute alcohol to obtain 0.60 g of a white solid substance (compound 2) with a yield of 30.0%.

Compound 2

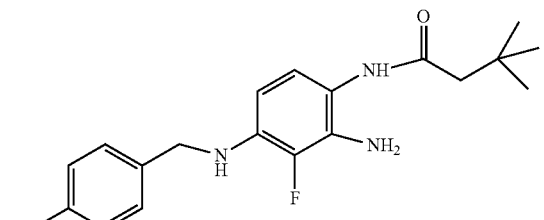

The white solid substance has a melting point of 162.9-163.4° C.; an ESI mass spectroscopic analysis of [M+H]$^+$ 398.2.

Embodiment 3

Synthesis of the Compound 3 (N-(2-amino-3-fluoro-4-(4-trifluoromethyl benzylamino)-phenyl)-cyclopentyl Formamide)

The intermediate II (1.52 g, 5 mmol) and cyclopentyl formic acid (0.541 ml, 5 mmol) are dissolved in dry dichloromethane (20 ml), and EDC.HCl (1.88 g, 12.5 mmol) and DMAP (0.08 g, 0.1 mmol) are added for a reaction overnight at room temperature under stirring. After the reaction, a reaction solution is fully washed with water (20 ml×3) and dichloromethane is recovered under a reduced pressure; and an obtained solid is recrystallized with dilute alcohol to obtain 1.11 g of a white solid substance (compound 3) with a yield of 56.2%, and a melting point of 222.9-223.5° C.

Compound 3

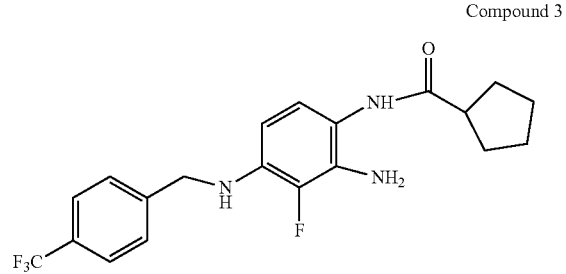 [SMILES: Nc1c(NC(=O)C2CCCC2)ccc(NCc2ccc(C(F)(F)F)cc2)c1F]

Embodiment 4

Synthesis of the Compound 4 (N-(2-amino-3-fluoro-4-(4-trifluoromethyl benzylamino)-phenyl)-cyclopentyl Acetamide)

The intermediate II (1.52 g, 5 mmol) and cyclopentyl acetic acid (0.582 ml, 5 mmol) are dissolved in dry dichloromethane (20 ml), and EDC.HCl (0.6 g, 5 mmol) and DMAP (0.32 g, 2.0 mmol) are added for a reaction overnight at room temperature under stirring. After the reaction, a reaction solution is fully washed with water (20 ml×3) and dichloromethane is recovered under a reduced pressure; and an obtained solid is recrystallized with dilute alcohol to obtain 0.93 g of a white solid substance (compound 4) with a yield of 45.4%, and a melting point of 196.9-197.5° C.

Compound 4

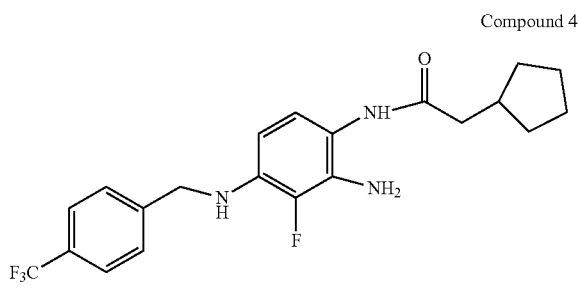 [SMILES: Nc1c(NC(=O)CC2CCCC2)ccc(NCc2ccc(C(F)(F)F)cc2)c1F]

Embodiment 5

Synthesis of the Compound 5 (N-(2-amino-3-fluoro-4-(4-trifluoromethyl benzylamino)-phenyl)-3-piperidinyl-1-propionamide)

The intermediate II (1.52 g, 5 mmol) and 1-piperidine propionic acid (0.786 mg, 5 mmol) are dissolved in dry dichloromethane (20 ml), and EDC.HCl (1.2 g, 10 mmol) and DMAP (0.4 g, 2.5 mmol) are added for a reaction overnight at room temperature under stirring. After the reaction, a reaction solution is fully washed with water (20 ml×3) and dichloromethane is recovered under a reduced pressure; and an obtained solid is recrystallized with dilute alcohol to obtain 1.36 g of a white solid substance (compound 5) with a yield of 62.3%, and a melting point of 202.1-203.5° C.

Compound 5

Embodiment 6

Synthesis of the Compound 6 (N-(2-amino-3-fluoro-4-(4-trifluoromethyl benzylamino)-phenyl)-3-furanyl-2-propanamide)

The intermediate II (1.52 g, 5 mmol) and 3-(2-furan) propionic acid (0.695 mg, 5 mmol) are dissolved in dry dichloromethane (20 ml), and EDC.HCl (1.2 g, 10 mmol) and DMAP (0.4 g, 2.5 mmol) are added for a reaction overnight at room temperature under stirring. After the reaction, a reaction solution is fully washed with water (20 ml×3) and dichloromethane is recovered under a reduced pressure; and an obtained solid is recrystallized with dilute alcohol to obtain 0.69 g of a white solid substance (compound 6) with a yield of 33.0%, and a melting point of 212.2-213.5° C.

Compound 6

Embodiment 7

Synthesis of the Compound 7 (N-(2-amino-3-fluoro-4-(4-trifluoromethyl benzylamino)-phenyl)-4-phenyl Butylamine The intermediate II (1.52 g, 5 mmol) and phenylbutyric acid (0.821 mg, 5 mmol) are dissolved in dry dichloromethane (20 ml), and EDC.HCl (0.6 g, 5 mmol) and DMAP (0.8 g, 5 mmol) are added for a reaction overnight at room temperature under stirring. After the reaction, a reaction solution is fully washed with water (20 ml×3) and dichloromethane is recovered under a reduced pressure; and an obtained solid is recrystallized with dilute alcohol to obtain 0.93 g of a white solid substance (compound 7) with a yield of 41.6%, and a melting point of 198.5-199.5° C.

Compound 7

Embodiment 8 High-Throughput Determination of $Rb^+$ Efflux by Atomic Absorption Spectrometry (AAS)

The test is performed by the following method with the compound 1 as an example.

The determination technique of $Rb^+$ efflux by AAS is safer and faster in high-throughput screening of potassium channel regulators, and has the characteristics of directly reflecting the activity of ion channels and the regulatory role of regulators. Rb has a similar atomic size to K, and the potassium channel is permeable to $Rb^+$, the opening or closing of the potassium channel can be determined by measuring the concentration of $Rb^+$ efflux. Rb has a specific atomic absorption at 780 nm and the $Rb^+$ concentration can be measured by AAS. Therefore, AAS can be used to screen potassium channel openers or shutters by the high-throughput determination technique for measuring $Rb^+$ efflux.

Chinese hamster ovary (CHO) cells with stable KCNQ2/3 channels in logarithmic growth phase are inoculated on a 96-well plate at a density of $2\times10^4$ cells/well. Three wells are provided for each concentration. Solvent control wells having the corresponding concentrations are arranged. After adherent growth overnight, the culture medium is discarded, and 200 µl of a loading buffer containing RbCL is added, and culturing is performed at 37° C. and under 5% $CO_2$ for 3 h. The loading buffer is then discarded and washing is performed 3 times with a wash buffer. To screen the channel opener, the compound to be tested is diluted in a depolarizing buffer and 200 µl of the above solution is added into the cells and reacted for 10 min. After incubation for 10 min, 200 µl of a supernatant is carefully transferred into another 96-well plate. $Rb^+$ atomic absorption at 780 nm is determined by an ICR8000 atomic absorption spectrometer. The relative efflux is calculated according to the formula Fsupern=(Rb_supern/cpd/Rb_supern/d)*100.

The results show that the dose-dependent activation of the compound 1 to the CHO cells with stable KCNQ2/3 channels at concentrations of 0.03, 0.1, 0.3, 1, 3 and 10 µM respectively is determined by the determination technique of $Rb^+$ efflux by AAS. RTG is an experimental positive control Retigabine of $EC_{50}$=0.86±0.18 µM, and compound 1 is a test group of $EC_{50}$=0.15±0.04 µM. Thus, the compound 1 is a high activity opener for KCNQ2/3 potassium channels.

The results of high-throughput determination of $Rb^+$ efflux of some compounds are shown in Table 1. Table 1 shows that the compounds of the present invention have a certain potassium channel opening activity.

TABLE 1 performance test of some compounds

| Compound number | KCNQ2/3 $EC_{50}$ (µM) | Purity of compound (%) * | m/z (M + H) ** |
|---|---|---|---|
| 1 | 0.15 ± 0.04 | 99.5 | 424.2 |
| 2 | 0.21 ± 0.08 | 99.2 | 398.2 |
| 3 | 2.83 ± 0.21 | 99.1 | 396.4 |
| 4 | 0.58 ± 0.13 | 99.2 | 410.3 |
| 5 | 0.75 ± 0.12 | 99.0 | 439.2 |
| 6 | 3.58 ± 0.73 | 98.9 | 422.2 |
| 7 | 5.26 ± 0.82 | 99.3 | 446.2 |

* HPLC area normalization method
** ESI MS positive ion source Q1 full scan mode Embodiment 9 Electrophysiological Patch Clamp Determination The test is performed by the following method with the compound 1 as an example.

CHO cells culture: CHO cells with stable KCNQ channels are cultured in a DMEM culture solution containing 10% fetal bovine serum, 100 U/ml penicillin and streptomycin, and then digested and passaged by pancreatin. The cells are placed on a 12 mm round cover glass and cultured in a 24-well plate.

Cell membrane current record by patch clamp technique: HEKA-EPC10 is used as a patch clamp amplifier. Amphotericin B (final concentration of 0.1-0.2 mg/ml) is used in the electrode to record the perforation patch clamp. After polishing, the microelectrode is filled with an electrode inner fluid, and the resistance value is controlled to be 2-4 MΩ. The electrode inner fluid used for recording CHO cells is (mM): KCl 160, HEPES 5, $MgCl_2$ 3, $CaCl_2$ 1 and EGTA 3, and the pH is adjusted to 7.4 with KOH. The components of the extracellular fluid are (mM): NaCl 160, KCl 2.5, HEPES 10, glucose 8, $MgCl_2$ 1 and $CaCl_2$ 5. After forming a giant resistance seal between the microelectrode and the cell membrane, the current is recorded under voltage clamping.

Figure 2:
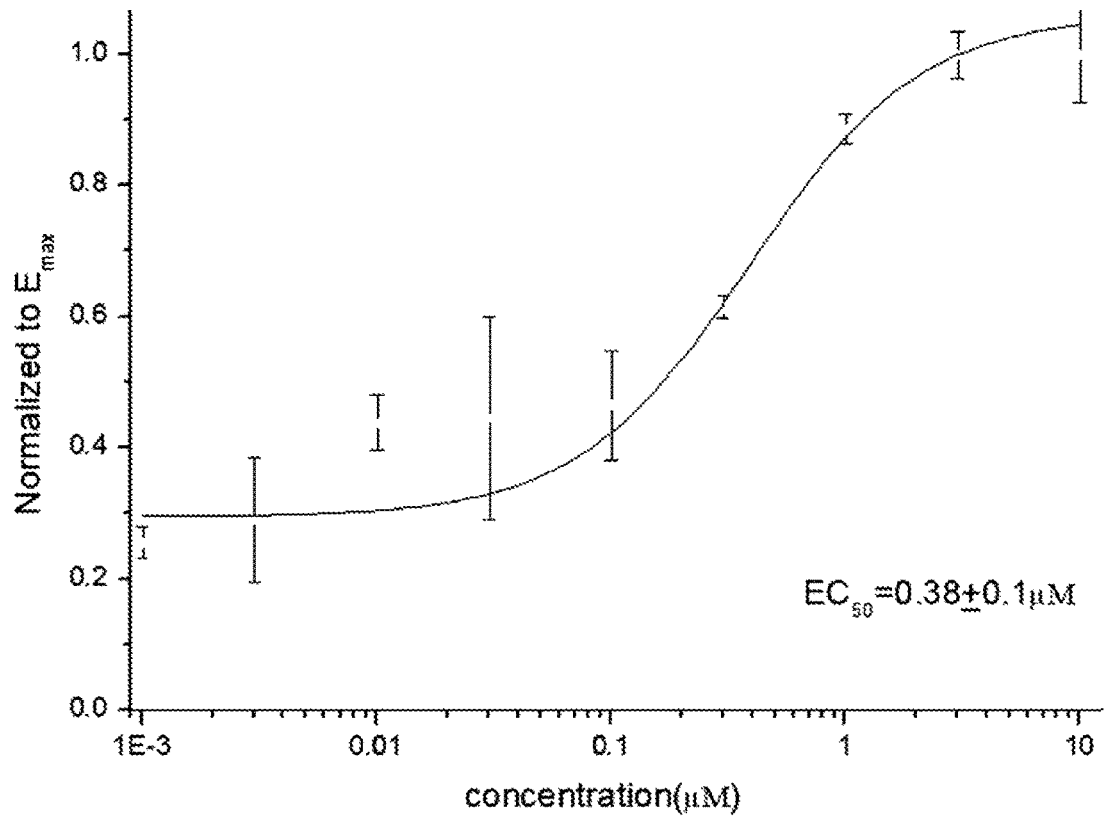
FIG. 2 is a diagram showing a dose-effect curve of the opening effect of the compound 1 on the KCNQ2/3 channels recorded by the whole-cell patch clamp.
Figure 3:
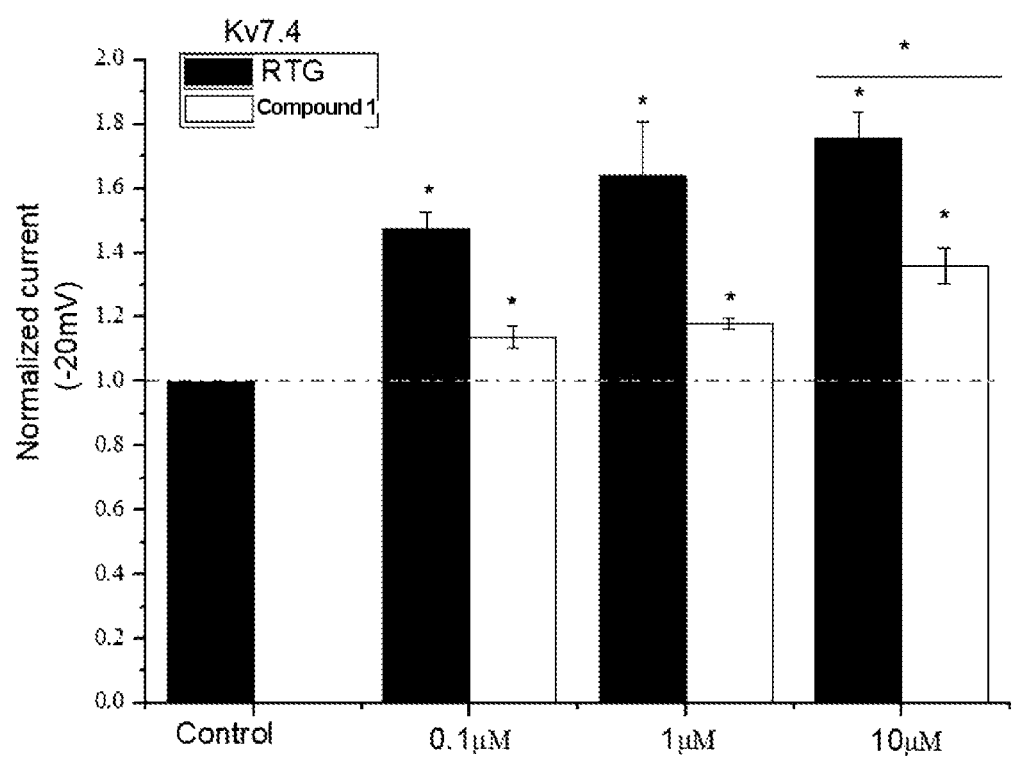
FIG. 3 is a diagram showing an opening effect of the compound 1 on a KCNQ4 (Kv7.4) channel subtype.

As shown in FIGS. 1-3, the compound 1 can significantly activate KCNQ2/3 (Kv7.2/7.3), and the $EC_{50}$ value is 0.38±0.10 µM, but its opening activity to KCNQ4 (Kv7.4) is relatively small. The compound 1 has good selectivity.

In view of the opening effects of the compounds of the present invention on KCNQ family potassium channels, they are considered useful for increasing the current of voltage-dependent potassium channels in mammals, such as humans, and can be applied for the treatment of diseases sensitive to the increase in currents of KCNQ family potassium channels, such as epilepsy, various anxiety disorders, and various neuropathic pain.

Embodiment 10 Maximum Electroshock Seizure (MES) Experimental Model

The compound 1 and compound 2 are taken as examples, and Retigabine (RTG) is used as a positive control drug.

Methods: Kunming mice, male, 18-22 g, are placed in the experimental environment 3 days before the experiment to make them adapt to the environment, eat and drink freely; the room temperature is 23-25° C.

The experimental instrument is YLS-9A physiological and pharmacological electronic stimulator: continuous wave output; wave width of 20 ms; gap of 10 ms; wave number of 70; voltage of 60 V; current limit of 3.5 mA.

Methods: 24 hours before the formal experiment, the mice are screened, the stimulator is set according to the above parameters, the mouse ears are clamped with crocodile clip of the stimulator, and the stimulation is started. The ankylosis of the hind limbs of the mice is taken as a positive index to screen the qualified (positive) mice and eliminate the substandard mice. In the formal experiment, the grouping is randomly performed with 10 mice in each group according to the experimental scheme, and the electrical stimulation is carried out. If no ankylosis is found in the hind limbs, it is effective (positive).

Results: the effective rate of the blank control group is 0%, the effective rate of the compound 1 is 100% (10/10) after intraperitoneal administration of 1 mg/kg body weight, the effective rate of the compound 2 is 90% (9/10) after intraperitoneal administration of 1 mg/kg body weight, and the effective rate of the positive control drug RTG is 80% (8/10) after intraperitoneal administration of 10 mg/kg body weight. The results show that the compounds of the present invention have the same obvious anticonvulsant characterization effect as RTG.

Embodiment 11 Pentylenetetrazole (PTZ)-Induced Epilepsy Model

The compound 1 is tested, and RTG is used as a positive control drug.

Experimental conditions: room temperature 25±1° C.

Experimental animals: KM mice, half male and half female, weighing 18-25 g, 10-12 mice in each group, adapt to the environment for 3 days and eat and drink freely.

Methods: the day before the experiment, each animal is labeled to ensure that the determination time of each animal after administration is consistent. The experimental animals fast for more than 8 h the night before the experiment. 25% hydroxypropyl β-cyclodextrin dissolved drugs are given intraperitoneally 15 min before the model is made. After the drugs are absorbed, the model is made by the subcutaneous administration of 85 mg/kg PTZ (administration volume of 0.1 ml/10 g) body weight to the neck and back. After PTZ administration, time is counted and the model is put into the transparent observation box in time to keep the environment quiet. The seizure threshold and the number of non-seizure animals are recorded. Each mouse is observed for 30 min (the threshold is the time from PTZ injection to the first occurred generalized clonus and loss of righting reflex of mice; if the animals do not have seizures within 30 min, the threshold is recorded as 30 min). The seizure threshold and the rate of non-death mice (i.e. protective rate) within 12 h after constructing the mold are compared.

Results: the model group (solvent group) has a seizure threshold of 465±394 s, and a protective rate of 16.7% (2/12); the positive control group (RTG) of 15 mg/kg body weight has a seizure threshold of 858.17±528.48 s, and a protective rate of 50% (6/12); the compound 1 of 5 mg/kg body weight has a seizure threshold of 1185.96±134.28 s, and a protective rate of 100% (20/20); the compound 1 of 3 mg/kg body weight has a seizure threshold of 867.21±152.51 s, and a protective rate of 100% (20/20); the compound of 1 mg/kg body weight has a seizure threshold of 1166.31±145.32 s, and a protective rate of 100% (20/20). The differences in the seizure thresholds and the protective rates between the compound 1 and the model group is statistically significant, and there is no significant difference between each administration group and the positive control group (15 mg/Kg) (P<0.05). The results show that the effects of the compounds of the present invention on PTZ-induced epilepsy are better than that of the positive control drug.

Embodiment 12

Tablets are prepared in accordance with a method known in the art, each tablet contains the following ingredients.

| | | |
|---|---|---|
| Compound 1 | 5 mg | |
| Lactose | 10 mg | |
| Magnesium stearate | 1 mg | |
| Polyvinylpyrrolidone | 15 mg | |

The embodiments listed in the present invention aim to clarify the derivatives disclosed in the present invention, the preparation method thereof and its obvious activation effect on KCNQ channel current. The embodiments are not merely illustrative of the specific compounds described herein as well as synthesis methods and pharmaceutical activity thereof, but may also be used to illustrate synthesis of homologues and analogs thereof by changing the type and amount of starting materials, which will not limit the scope of the present invention in any way.

What is claimed is:

1. A chemical compound, wherein a general chemical formula of the chemical compound is shown in formula I:

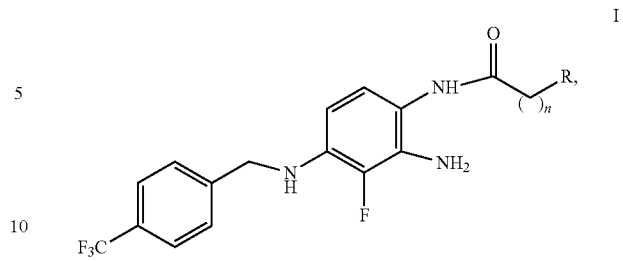

wherein R is cyclopentyl, and n=2 (compound 1); alternatively, R is tert-butyl, and n=1 (compound 2); structural formulas of the compound 1 and the compound 2 are as follows:

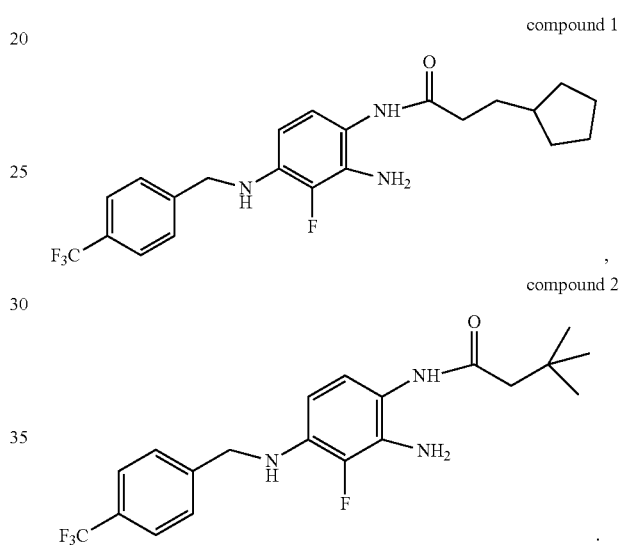

2. A preparation method of the chemical compound according to claim 1, comprising the following steps:
 (a) dissolving p-trifluoromethyl benzylamine and 2,3-difluoro-6-nitroaniline in anhydrous dimethyl sulfoxide (DMSO) for a first reaction under conditions of triethlamine as an acid-binding agent and iodine as a catalyst, to obtain 2-fluoro-4-nitro-N1-(4-trifluoromethyl-benzyl)-1,3-phenylenediamine;
 (b) putting the 2-fluoro-4-nitro-N1-(4-trifluoromethyl-benzyl)-1,3-phenylenediamine into a zinc powder saturated ammonium chloride system for a reduction reaction to obtain 3-fluoro-N4-(4-trifluoromethyl-benzyl)-1,2,4-benzenetriamine;
 (c) dissolving the 3-fluoro-N4-(4-trifluoromethyl-benzyl)-1,2,4-benzenetriamine and a cydopentyl- or tert-butyl-substituted carboxylic acid in a solvent to obtain a mixed solution, adding 1-ethyl-3-(3-dimethylaminopropyl)carbodiimide hydrochloride (EDC.HCl) and 4-dimethylaminopyridine (DMAP) in the mixed solution for a second reaction, separating a liquid after the second reaction is ended to obtain an organic layer, and extracting a target compound 1 from the organic layer; wherein, a molar ratio of the 3-fluoro-N4-(4-trifluoromethyl-benzyl)-1,2,4-benzenetriamine, the cydopentyl- or tert-butyl-substituted carboxylic acid, the EDC.HCl and the DMAP is 1:1:(1-2):(0.1-1).

3. A pharmaceutical composition, comprising the chemical compound according to claim 1 as an active ingredient, and one or more pharmaceutically acceptable carriers.

4. A method of opening a potassium channel, comprising the step of administering the chemical compound according to claim 1 to the potassium channel.

5. The method according to claim 4, wherein the potassium channel is a KCNQ2 or KCNQ3 potassium channel.

6. A method of treating epilepsy comprising the step of administering the chemical compound according to claim 1 to a patient to be treated.

7. A method of treating anxiety comprising the step of administering the chemical compound according to claim 1 to a patient to be treated.

8. A method of treating pain comprising the step of administering the chemical compound according to claim 1 to a patient to be treated.

* * * * *